United States Patent [19]

Haze et al.

[11] Patent Number: 5,623,069

[45] Date of Patent: Apr. 22, 1997

[54] METHOD FOR PRODUCING 5'-NUCLEOTIDE

[75] Inventors: Akira Haze, Kawanishi; Hiroyuki Hatano, Kakogawa; Tomomi Ikemoto, Kamigohri-cho; Yoshifumi Kitamoto, Kakogawa, all of Japan

[73] Assignee: Takeda Chemical Industries, Ltd., Osaka, Japan

[21] Appl. No.: 437,984

[22] Filed: May 10, 1995

Related U.S. Application Data

[63] Continuation of Ser. No. 87,047, Jul. 7, 1993, abandoned.

[30] Foreign Application Priority Data

Jul. 8, 1992 [JP] Japan ..................... 4-181145

[51] Int. Cl.⁶ ..................... C07H 1/00; C07H 19/06; C07H 19/16
[52] U.S. Cl. ..................... 536/26.71; 536/26.72; 536/26.73; 536/26.74; 536/26.8
[58] Field of Search .................. 536/26.1, 26.71, 536/26.72, 26.74, 26.9, 26.73, 26.8

[56] References Cited

U.S. PATENT DOCUMENTS

| 3,413,282 | 11/1968 | Yoshikawa et al. | 536/26.71 |
| 3,433,783 | 3/1969 | Honja et al. | 536/26.71 |
| 3,444,158 | 5/1969 | Honjo et al. | 536/26.71 |

FOREIGN PATENT DOCUMENTS

| 0453597 | 4/1990 | European Pat. Off. | 536/26.71 |
| 59-080694 | 5/1984 | Japan . | |
| 59-167599 | 9/1984 | Japan . | |
| 59-163397 | 9/1984 | Japan . | |

*Primary Examiner*—James O. Wilson
*Attorney, Agent, or Firm*—Wenderoth, Lind & Ponack

[57] ABSTRACT

A method of producing 5'-nucleotide, which comprises maintaining a nucleoside suspension in an organic solvent at a temperature not lower than about 20° C., and then subjecting the resultant suspension to a phosphorylatipon of the nucleoside(s).

According to the present invention, 5'-nucleotide can be produced from a nucleoside at high purity and high yield in a shortened reaction time, and impurity removal in the nucleotide purification process is easily accomplished.

9 Claims, No Drawings

METHOD FOR PRODUCING 5'-NUCLEOTIDE

This application is a continuation of now abandoned application Ser. No. 08/087,047, filed Jul. 7, 1993, now abandoned.

DESCRIPTION OF THE PRESENT INVENTION

1. Field of the Invention

The present invention relates to an improved method of nucleoside phosphorylation, more specifically to a method of nucleoside phosphorylation wherein a nucleoside is heated in an organic solvent, to transform its crystal form, and then phosphorylated with its hydroxyl group remaining unprotected.

The present method offers economical production, on an industrial scale, of 5'-nucleotide (or its mixture), which is useful in seasonings and pharmaceuticals, particularly as a single substance or in a mixture including inosinic acid, guanylic acid, or cytidylic acid or other substances.

2. Prior Art

Conventional methods of chemically phosphorylating nucleosides include the following.

1) A method of reacting a nucleoside with a phosphorous oxychloride in a trialkyl phosphate (U.S. Pat. No. 3,413,282).
2) A method of using mixed crystals of guanosine and inosine (Japanese Patent Unexamined Publication No. 167599/1984).
3) A method of using mixed phosphorylation of inosine and guanosine (EPA-453,597).
4) A method of using a metallizing agent in phosphorylation (Japanese Patent Unexamined Publication No. 80694/1984).
5) A method of using an aluminizing agent in phosphorylation (Japanese Patent Unexamined Publication No. 163397/1984).

The following are known as to the chemical phosphorylation of nucleosides relating to the object of the present invention.

When a nucleoside, e.g., mixed crystals of inosine and guanosine, are phosphorylated with phosphorus oxychloride in the presence of triethyl phosphate, diphosphates, hypoxanthine, guanine, other by-products are produced upon obtaining the desired 5'-mononucleotide mixture, because inosine and guanosine differ in their phosphorylation rates; specifically, the phosphorylation rate of guanosine is about ⅓ of that of inosine.

As a means of suppressing this production of by-products, mixed crystals of guanosine and inosine are used in phosphorylation, as in method 2 above.

In another means of phosphorylation of an alkali metal salt of inosine or guanosine, as in method 3 above, the latter's phosphorylation is followed by the addition of the former to achieve sequential phosphorylation.

In still another means of nucleoside phosphorylation, a metallizing agent or aluminizing agent is used to activate the hydroxyl group of the nucleoside, followed by phosphorylation, as in methods 4 and 5 above.

However, with respect to yield, by-product production, operation and other features from an industrial viewpoint, there is no satisfactory method of nucleotide production from a nucleoside based on, e.g., chemical phosphorylation of a mixture containing inosine and guanosine in a given ratio or mixed crystals of inosine and guanosine. There is therefore a need for the development of a method of producing 5'-nucleotide with high purity, high yield and minimal by-products, in a shortened reaction time.

SUMMARY OF THE INVENTION

The present invention is to provide a method of producing 5'-nucleotide, which comprises maintaining a nucleoside suspension in an organic solvent at a temperature not lower than about 20° C., and then subjecting the resultant suspension to a phosphorylation of the nucleoside(s).

DETAILED DESCRIPTION OF THE PREFERRED EMBODIMENT

In the present invention, a nucleoside is defined as a sugar bound to a purine base or pyrimidine base via a glucoside bond, specifically ribonucleoside or deoxyribonucleoside. Examples of ribonucleoside include inosine, guanosine, cytidine, adenosine and uridine. Examples of deoxyribonucleoside include deoxyinosine, deoxyguanosine, deoxycytidine and deoxyuridine. Ribonucleoside is preferably used, with greater preference given to inosine and guanosine.

As the starting material nucleoside, the above nucleosides may be used singly or in mixture. The nucleosides may be used as salts thereof. Examples of nucleoside salts include those with inorganic bases (e.g., alkali metals such as sodium and potassium, alkaline earth metals such as calcium and magnesium, and ammonia), those with organic bases (e.g., trialkylamines such as trimethylamine and triethylamine, and pyridine), those with inorganic acids (e.g., hydrochloric acid, phosphoric acid, hydrobromic acid, sulfuric acid) and those with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid).

It is preferable to use mixed crystals of inosine and guanosine as the starting material nucleoside. The mixed crystals can be obtained by a known method. For example, mixed crystals obtained by crystallizing the solute from an aqueous solution containing inosine and guanosine can be used (see Japanese Patent Examined Publication No. 38199/1972). In this case, crystallization can be achieved by cooling, concentration, addition of seed crystal, addition of a hydrophilic solvent which does not dissolve nucleoside (e.g., acetone), pH adjustment (from an acidic range of pH 3 or below or alkaline range of pH 9 or higher, where nucleoside solubility is high, to pH between 3 and 9), or combinations thereof. Desirably, after the mixed nucleoside crystals are crystallized from the nucleoside-containing solution by such a method, the mixed crystals are separated by a commonly used method such as aspiration, pressure filtration, centrifugation or centrifugal precipitation, followed by, e.g., thermal drying under reduced pressure, to remove the solvent (e.g., water), after which it is subjected to phosphorylation.

Any organic solvent can be used for the present invention, as long as it does not interfere with the reaction. This organic solvent is preferably a polar solvent, e.g., a tri-lower ($C_{1-6}$) alkyl phosphate such as trimethyl phosphate or triethyl phosphate, a tri-lower ($C_{1-6}$) alkoxy lower ($C_{1-6}$) alkyl phosphate such as trimethoxyethyl phosphate or triethoxyethyl phosphate, a sulfoxide such as dimethylsulfoxide, or an amide such as dimethylformamide or N-dimethylacetamide. These organic solvents may be used singly or in combination. Of these, tri-lower ($C_{1-6}$) alkyl phosphates are preferred, with greater preference given to triethyl phosphate and trimethyl phosphate.

Although the weight amount of organic solvent used varies depending on the type thereof, it is appropriately chosen over the range of from about 5 to about 20 times, preferably about 8 to about 17 times, that of nucleoside.

In the present invention, phosphorylation is carried out as follows. First, a nucleoside or a salt thereof is suspended in an organic solvent, and then an obtained suspension is maintained at a temperature not less than about 20° C. The temperature is preferably about 20° to about 100° C., more preferably about 30° to about 80° C., most preferably about 40° to about 60° C. The time for maintaining the suspension at a temperature not lower than 20° C. varies depending on the temperature, the amount of the starting material nucleoside described above. The time is preferably about 10 to about 120 minutes, more preferably about 10 to about 60 minutes, most preferably about 10 to about 20 minutes. Generally, because phosphorylation is a liquid-liquid reaction following dissolution of a nucleoside, the reaction rate varies depending on the grain size and form of the nucleoside crystal used for the reaction. Because the finer the nucleoside crystal grains, the greater the surface area, the apparent reaction rate can be increased by reducing the nucleoside crystal grain size. The nucleoside crystal grain size is preferably about 1 to about 1000 μm, more preferably about 20 to about 500 μm.

However, in the present invention, a nucleoside crystal may be of any grain size and form in maintaining a nucleoside suspension in an organic solvent at a temperature not lower than 20° C. Because the nucleoside crystal changes to an apparently amorphous crystal upon heating, due to a phenomenon resembling crystal transition, the nucleoside crystal surface area increases and the rate of reaction with phosphorylating agent increases.

Subsequently, the resultant suspension is subjected to a phosphorylation of nucleoside(s). The phosphorylation of nucleoside(s) is carried out by using a phosphorylating agent. Reaction temperature is preferably about −30° to about 10° C., more preferably about 0° to about 10° C.

The phosphorylating agent used for the present invention is a phosphorylating agent commonly used for phosphorylation, preferably a phosphorus oxyhalogenide such as phosphorus oxychloride or phosphorus oxybromide.

In phosphorylation, it is preferable to use the phosphorus oxyhalogenide after conversion to a partial hydrate, rather than as such, since it usually offers higher selectivity for 5'-mononucleotide production and reduces the production of by-products such as 2'- or 3'-monophosphate and diphosphates.

To obtain a hydrate of phosphorus oxyhalogenide, the phosphorus oxyhalogenide is dissolved in a reaction solvent as described above and then reacted with a small amount of water or an alcohol such as methanol, ethanol or tertiary butanol.

The molar amount of phosphorus oxyhalogenide used is normally about 1 to about 5 times, preferably about 1.5 to about 4 times, that of nucleoside. Amounts outside of this range are typically undesirable, since extremely lesser amounts result in residence of unreacted nucleoside, and extremely greater amounts result in production of by-product diphosphates and lowered yield of the desired 5'-mononucleotide. Usually, the amount of addition is appropriately chosen over the above content range on the basis of the type of phosphorylating agent or solvent and other factors.

Although reaction time varies depending on the kind of solvent, the presence or absence of a reaction accelerator (e.g., extremely lesser amount of sodium hydroxide etc.) and other factors, it is usually about 30 minutes to about 10 hours. In the present method of phosphorylation, the reaction proceeds to completion in a shorter time, in comparison with conventional methods of phosphorylation.

The reaction product thus obtained is mixed with cold water (e.g., not higher than about 10° C., preferably not higher than about 5° C.) by a conventional method to hydrolyze the unreacted phosphorylating agent and resulting nucleoside phosphohalogenate to yield a solution (hydrolyzate) containing 5'-nucleotide.

The 5'-nucleotide thus obtained can be purified by conventional methods:

1) a method wherein the hydrolyzate is adjusted to a pH of about 1.5 with sodium hydroxide and then treated with activated charcoal, 2) a method wherein the reaction solvent is extracted and separated using another organic solvent, after which the residue is neutralized with an alkali such as sodium hydroxide and then purified by resin adsorption or crystallization, and 3) a method wherein the reaction solvent is extracted and separated using another organic solvent, after which the residue is treated with activated charcoal. Following any of these purifying methods, the desired product can be obtained as mixed crystals of disodium nucleoside-5'-phosphates by a conventional method.

According to the present invention, 5'-nucleotide can be produced from nucleoside at high purity and high yield, nucleoside phosphorylation time is shortened, and impurity removal in the nucleotide purification process is easily accomplished. The amount of phosphorous oxyhalogenide is much lower than usual usage of it.

EXAMPLES

The present invention is hereinafter described in more detail by means of the following working examples.

In the examples below, $IMPNa_2$ represents disodium inosine-5'-monophosphate; $GMPNa_2$, disodium guanosine-5'-monophosphate; IR, inosine; GR, guanosine; TEP, triethyl phosphate; HLC, high performance liquid chromatography.

Working Example 1

Phosphorylation of inosine-guanosine mixed crystal

A mixed crystalline powder of inosine and guanosine (85.3 g of inosine and 103.6 g of guanosine) was suspended in 2106.2 g of triethyl phosphate at a room temperature (about 18° C.) and cooled to about 5° C., after which the resultant suspension was subjected to a phosphorylation of nucleosides by adding 294.3 g of phosphorus oxychloride and 11.3 g of water for 3.5 hours.

Separately, another mixed crystalline powder of inosine and guanosine (85.3 g of inosine and 103.6 g of guanosine) was suspended in 2106 g of triethyl phosphate at a room temperature (about 18° C.) in the same manner as above. The resultant suspension was heated to 50° C. and stirred for 15 minutes, after which it was subjected to a phosphorylation of nucleosides by adding 294.3 g of phosphorus oxychloride and 11.3 g of water for 3.5 hours while cooling at about 5° C.

Subsequently, each reaction mixture was added to 3211 g of water (about 5° C.) and hydrolyzed. The resulting hydrolyzates were assayed by HLC. The results are given in Table 1.

Conditions of quantitative analysis by HLC are as follows (the same applies to the examples below), 1) Quantitative analysis of $IMPNa_2$ and $GMPNa_2$ Apparatus: HPLC (LC-4A, Shimadzu Corporation, Japan)

Column: Anion exchange resin (CDR10, Mitsubishi Chemical, Japan) 4.5 mm dia.×25 mm length Eluent: 0.5 mol/liter acetate buffer comprising 0.3 mol/liter acetic acid and 0.2 mol/liter ammonium acetate Flow rate: 1.8 ml/min 2) Quantitative analysis of unreacted IR and unreacted GR Apparatus: HPLC (LC-6A, Shimadzu Corporation, Japan)

Column: Cation exchange resin (CK-10U, Mitsubishi Chemical, Japan) 4.5 mm dia.×25 mm length Eluent: 0.15 mol/liter acetate buffer comprising 0.15 mol/liter ammonium acetate.

Flow rate: 0.45 ml/min

TABLE 1

|  | With TEP and Heating | With TEP and without Heating |
|---|---|---|
| $IMPNa_2$ yield | 93.1 mol % | 91.6 mol % |
| $GMPNa_2$ yield | 90.4 mol % | 86.5 mol % |
| Unreacted IR concentration | 0.32 mg/g | 0.61 mg/g |
| Unreacted GR concentration | 1.29 mg/g | 2.52 mg/g |

Working Example 2

Phosphorylation of simple crystal of inosine or guanosine

A crystalline powder of each of inosine and guanosine (85.3 g of inosine and 103.6 g of guanosine) was suspended in triethyl phosphate at a room temperature (about 18° C.) in the same manner as in Example 1. Each resulting reaction mixture, with or without heating, was assayed by HLC. The results are given in Table 2.

TABLE 2

|  | With TEP and Heating | With TEP and without Heating |
|---|---|---|
| $IMPNa_2$ yield | 92.9 mol % | 90.8 mol % |
| $GMPNa_2$ yield | 92.5 mol % | 83.5 mol % |
| Unreacted IR concentration | 0.23 mg/g | 0.58 mg/g |
| Unreacted GR concentration | 0.43 mg/g | 2.15 mg/g |

Working Example 3

Comparison of heating conditions (heating temperature) in the presence of TEP

A mixed crystalline powder of inosine and guanosine (85.3 g of inosine and 103.6 g of guanosine) was suspended in 2106.2 g of triethyl phosphate at a room temperature (about 18° C.) and heated at 25°, 50° or 100° C. for 15 minutes, after which the resultant suspension was cooled to about 5° C. and then subjected to a phosphorylation of nucleosides by adding 294.3 g of phosphorus oxychloride and 11.3 g of water for 3.5 hours.

Subsequently, each reaction mixture was added to 3211 g of water (about 5° C.) and hydrolyzed. The resulting hydrolyzates were assayed by HLC. The results are given in Table 3.

TABLE 3

Comparison of Heating Temperatures in the Presence of TEP (Heating time 15 minutes)

| Heating Temperature | Yield | |
|---|---|---|
|  | $IMPNa_2$ (mol %) | $GMPNa_2$ (mol %) |
| 25° C. | 91.2 | 85.3 |
| 50° C. | 91.1 | 89.4 |
| 100° C. | 90.6 | 87.5 |

Working Example 4

Comparison of heating conditions (heating time) in the presence of TEP

The procedure of Example 3 was followed but heating in the presence of triethyl phosphate was conducted at 50° C. for 15, 30 or 60 minutes. The obtained reaction mixture was assayed by HLC. The results are given in Table 4.

TABLE 4

Comparison of Heating Times in the Presence of TEP (Heating temperature 50° C.)

| Heating Time | Yield | |
|---|---|---|
|  | $IMPNa_2$ (mol %) | $GMPNa_2$ (mol %) |
| 15 minutes | 91.1 | 89.4 |
| 30 minutes | 90.5 | 89.2 |
| 60 minutes | 90.6 | 89.3 |

Working Example 5

Comparison of an addition amount of phosphorous oxyhalogenide

A mixed crystalline powder of inosine and guanosine (85.3 g of inosine and 103.6 g of guanosine) was suspended in 2106.2 g of triethyl phosphate at a room temperature (about 18° C.) and heated to 50° C. and stirred for 15 minutes, after which the resultant suspension was cooled to about 0° C. and then subjected to a phosphorylation of nucleosides by adding each 1.4, 1.6, 1.8, 2.0 or 2.75 times molar amount of phosphorous oxychloride and each 5.4, 7.2, 7.2, 9, 11.3 g of water for 3.5 hours.

Subsequently, each reaction mixture was added to 3211 g of water (about 5° C.) and hydrolyzed. The resulting hydrolyzates were assayed by HLC. The results are given in Table 5.

TABLE 5

| | Amount of phosphorous oxychloride (molar amount per one molar nucleoside) | | | | |
|---|---|---|---|---|---|
| | 1.4 | 1.6 | 1.8 | 2.0 | 2.75 |
| IMPNa$_2$ yield (mol %) | 88.3 | 90.5 | 90.9 | 91.2 | 91.5 |
| GMPNa$_2$ yield (mol %) | 88.2 | 90.5 | 90.5 | 90.6 | 91.0 |
| Unreacted IR concentration (mg/g) | 1.9 | 0.9 | 0.6 | 0.6 | 0.5 |
| Unreacted GR concentration (mg/g) | 3.2 | 1.8 | 1.4 | 1.4 | 0.4 |

Working Example 6

Comparison of conditions in phosphorylation

A mixed crystalline powder of inosine and guanosine (85.3 g of inosine and 103.6 g of guanosine) was suspended in 2106.2 g of triethyl phosphate at a room temperature (about 18° C.) and heated to 50° C. and stirred for 15 minutes, after which the resultant suspension was cooled to about −5°, 0° or 5° C. and then subjected to a phosphorylation of nucleosides by adding 1.8 times molar amount of phosphorous oxychloride and 7.2 g of water for 3.5 hours.

Subsequently, each reaction mixture was added to 3211 g of water (about 5° C.) and hydrolyzed. The resulting hydrolyzates were assayed by HLC. The results are given in Table 6.

TABLE 6

| | Yield (mol %) | | Concentration (mg/g) | |
|---|---|---|---|---|
| | IMPNa$_2$ | GMPNa$_2$ | Unreacted IR | Unreacted GR |
| Reaction temperature: 5° C. Reaction time: 2 hours | 88.6 | 90.4 | 0.9 | 2.8 |
| Reaction temperature: 0° C. Reaction time: 3 hours | 90.9 | 90.5 | 0.6 | 1.4 |
| Reaction temperature: −5° C. Reaction time: 5 hours | 91.4 | 89.1 | 0.7 | 2.8 |

What is claimed is:

1. A method for producing a 5'-nucleotide, which consists essentially of:
   a pre-heating step of treating a nucleoside suspension in an organic solvent consisting of a tri-lower (C$_{1-6}$)alkyl phosphate at about 30° C. to 80° C. for about 10 to 120 minutes, the nucleoside being selected from the group consisting of inosine, guanosine, and mixed crystals of inosine and guanosine, to change the suspended nucleoside to an amorphous crystal form, and then
   a phosphorylating step of contacting the pre-treated nucleoside suspension with a phosphorous oxyhalogenide at about −30° C. to 10° C., thereby producing a 5'-nucleotide.

2. The method according to claim 1, wherein the tri-lower (C$_{1-6}$)alkyl phosphate is a triethyl phosphate.

3. The method according to claim 1, wherein the phosphorous oxyhalogenide is a phosphorous oxychloride.

4. The method according to claim 1, wherein the phosphorous oxyhalogenide is used in an amount of about 1 to about 5 moles per nucleoside.

5. The method according to claim 1, wherein the nucleoside is inosine.

6. The method according to claim 1, wherein the nucleoside is guanosine.

7. The method according to claim 1, wherein the nucleoside is mixed crystals of inosine and guanosine.

8. The method according to claim 1, wherein the pre-heating step is conducted at a temperature of about 40° C. to 60° C.

9. The method according to claim 1, wherein the pre-heating step is conducted for about 10 to 20 minutes.

* * * * *